US011795527B2

(12) United States Patent
Yadav et al.

(10) Patent No.: US 11,795,527 B2
(45) Date of Patent: Oct. 24, 2023

(54) PT—CO BASED ALLOY FOR MEDICAL USE

(71) Applicant: TANAKA KIKINZOKU KOGYO K.K., Tokyo (JP)

(72) Inventors: Shubham Yadav, Isehara (JP); Yuya Kato, Isehara (JP); Kenji Goto, Isehara (JP); Kunihiro Shima, Isehara (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 219 days.

(21) Appl. No.: 17/295,778

(22) PCT Filed: Nov. 18, 2019

(86) PCT No.: PCT/JP2019/045003
§ 371 (c)(1),
(2) Date: May 20, 2021

(87) PCT Pub. No.: WO2020/105570
PCT Pub. Date: May 28, 2020

(65) Prior Publication Data
US 2022/0017996 A1    Jan. 20, 2022

(30) Foreign Application Priority Data
Nov. 22, 2018 (JP) ................. 2018-219040

(51) Int. Cl.
*C22C 19/07* (2006.01)
*A61L 31/02* (2006.01)

(52) U.S. Cl.
CPC ............ *C22C 19/07* (2013.01); *A61L 31/022* (2013.01)

(58) Field of Classification Search
CPC ......... A61K 6/844; A61L 31/022; A61N 1/05; C22C 19/07; C22C 30/00; C22C 5/04
USPC ....................................... 420/438
See application file for complete search history.

(56) References Cited

U.S. PATENT DOCUMENTS

| | | | |
|---|---|---|---|
| 5,891,191 | A | 4/1999 | Stinson |
| 2012/0123525 | A1 | 5/2012 | Kramer-Brown et al. |
| 2013/0289704 | A1 | 10/2013 | Thompson |
| 2013/0289705 | A1 | 10/2013 | Thompson |
| 2017/0135831 | A1 | 5/2017 | Thompson |
| 2020/0038207 | A1* | 2/2020 | Simpson ............... C22C 1/0433 |

FOREIGN PATENT DOCUMENTS

| | | |
|---|---|---|
| JP | H586456 A | 4/1993 |
| JP | H10-43314 A | 2/1998 |
| JP | 2015-517035 A | 6/2015 |

OTHER PUBLICATIONS

Extended European Search Report issued in corresponding European Patent Application No. 19886348.2, dated Oct. 7, 2022.
International Searching Authority, "International Search Report," issued in connection with International Patent Application No. PCT/JP2019/045003, dated Feb. 10, 2020.
International Searching Authority, "Written Opinion," issued in connection with International Patent Application No. PCT/JP2019/045003, dated Feb. 10, 2020.
Japanese Office Action issued in connection with JP Appl. Ser. No. 2020-558362 dated Mar. 6, 2023.
Office Action issued in corresponding Japanese Patent Application No. 2020-558362, dated Jun. 5, 2023.

\* cited by examiner

*Primary Examiner* — Jie Yang
(74) *Attorney, Agent, or Firm* — Foley & Lardner LLP

(57) ABSTRACT

The present invention relates to an alloy for medical use, including Pt, Co, Cr, Ni, and Mo. The alloy includes 10 atom % or more and 30 atom % or less of Pt, 20 atom % or more and 31 atom % or less of Cr, 5 atom % or more and 24 atom % or less of Ni, 4 atom % or more and 8 atom % or less of Mo, the balance Co, and unavoidable impurities, and a ratio of the Ni content ($C_{Ni}$) to the Pt content ($C_{Pt}$), $C_{Ni}/C_{Pt}$ is 1.5 or less. The present invention can be applied to various kinds of devices for medical use, such as catheter, embolic coils, and guide wires, in addition to stents such as flow-diverter stents.

17 Claims, No Drawings

PT—CO BASED ALLOY FOR MEDICAL USE

CROSS-REFERENCE TO RELATED APPLICATIONS

The present application claims priority under 37 U.S.C. § 371 to International Patent Application No. PCT/JP2019/045003, filed Nov. 18, 2019, which claims priority to and the benefit of Japanese Patent Application No. 2018-219040, filed on Nov. 22, 2018. The contents of these applications are hereby incorporated by reference in their entireties.

TECHNICAL FIELD

The present invention relates to a metal alloy for medical use, which is suitable as a constituent material for various kinds of implant medical devices such as a stent, an aneurysm coil, a vena cava filter, a graft, and a pacemaker, or as a constituent material for various kinds of medical devices such as a catheter, a guide wire, and a stent retriever. In particular, the present invention relates to an medical alloy that is excellent in the mechanical properties, X-ray visibility, and workability required to ensure the function of the medical devices.

BACKGROUND ART

Various kinds of metal materials have been conventionally known as the constituent materials for medical devices such as various kinds of stents, an aneurysm coil, and a catheter. For example, a Co—Cr based medical alloy, which is defined in ASTM F562, is known. A Co—Cr based alloy known as a 35NLT alloy (Cr: 19 to 21% by mass, Ni: 33 to 37% by mass, Mo: 9 to 10.5% by mass, and the balance: Co) that satisfies this standard has been used in an artificial joint, a stent, or the like in recent years. As another example of the Co—Cr-based medical alloy, Patent Document 1 is also mentioned. Further, as medical alloys other than the Co—Cr based alloy, a SUS based alloy and a Ni—Ti based alloy, which are defined in ASTM A276, have also been known for a long time.

RELATED ART DOCUMENT

Patent Document

Patent Document 1: JP H10-043314 A

SUMMARY OF THE INVENTION

Problems to be Solved by the Invention

In an medical alloy, which constitutes a medical device, various characteristics are required in consideration of the application, the use mode, and the like. Specifically, as will be described below, chemical stability (corrosion resistance), mechanical properties (strength, elastic modulus, and the like), X-ray visibility (X-ray absorption coefficient), and workability are required.

A medical device is a device that comes into direct contact with the human body and is occasionally embedded in the human body. Therefore, chemical stability (corrosion resistance) is required. Further, for a medical device that is inserted and placed in a blood vessel that permanently pulsates and beats, such as a stent, high mechanical properties are also required. Furthermore, the examination and treatment with the use of a medical device such as a catheter, a stent, or an aneurysm coil are performed by insertion of the medical device into the human body and confirmation of the position of the device while X-ray imaging is performed. Therefore, it is preferable that the medical material has X-ray visibility.

In addition, a medical device such as a stent or a catheter is produced by the processing of the medical material into an extra-fine wire/extra-thin material, and then by the secondary processing of the extra-fine wire/extra-thin material into a stent tube shape, a coil shape, a bulb shape, or the like with the weaving, coiling, extruding, laser processing, or the like. Therefore, the medical alloy is also required to have high workability.

The above-described conventional alloys for medical use satisfy certain requirements as the constituent materials for various kinds of medical devices. In particular, the above-described 35NLT alloy being a Co—Cr based alloy is an alloy having high strength and high corrosion resistance, and has a track record of application to a stent or the like due to the characteristics.

However, a Co—Cr based alloy such as a 35NLT alloy does not satisfy all of the above-described required characteristics. As for the X-ray visibility, there is a problem that the Co—Cr based alloy is insufficient. Therefore, when the Co—Cr based alloy is applied to a stent, a metal having favorable X-ray visibility (Pt—W alloy or the like) is partially woven or welded to impart the X-ray visibility to the stent.

Further, a medical device such as a stent or a catheter and a treatment method using such a medical device have still been improved and newly developed also at present, and the application ranges have been expanded. Along with this, the above-described characteristics required for an medical alloy have become higher.

For example, in recent years, flow-diverter implantation is expected to become widespread as a treatment method for unruptured cerebral aneurysm. This treatment method is a method in which a stent (low-diverter stent) woven at high density with an extra-fine wire is placed in a blood vessel so as to cover the way in a cerebral aneurysm. By the placement of a flow-diverter stent, the blood flow into a cerebral aneurysm is reduced, and the cerebral aneurysm can be minified by turning into thrombus. This flow-diverter stent is required to exhibit the flexibility when being placed in a blood vessel and the adequate strength and elasticity for staying stably in the blood vessel without moving after the placement. Further, in the production of a flow-diverter stent, the extra-fine wire processing is required, and the workability higher than ever before is also required.

In addition, a balloon-expandable stent is used for the treatment of atherosclerosis or the like. In this medical device, the stent is plastically deformed when the balloon is expanded, and therefore, appropriate yield stress and high X-ray visibility are required. Further, the high elastic property and rupture stress are required in order to appropriately support the blood vessel in a lesion site after the stent expansion.

When the application to the latest medical device such as the flow-diverter stent described above is considered, a conventional alloy such as a Co—Cr based alloy can not always sufficiently meet such demands. The present invention has been made under such circumstances, and an object of the present invention to provide an alloy having excellent characteristics in the mechanical properties, X-ray visibility, workability, and the like required for the medical alloy. In particular, a device suitable for the medical alloy, such as a flow-diverter stent or the like, which requires a higher degree of radial force and improved visibility in the above characteristics, will be disclosed.

Means for Solving the Problems

In order to solve the above problems, the present inventors have simulated the characteristics practically required in a medical device such as a flow-diverter stent based on the shape/form, the use mode, the use conditions, and the like. The material characteristics based on the analysis results will be described later, and the present inventors have considered that for the suitable medical alloy, development of an alloy having a higher elastic modulus (Young's modulus) and a higher elastic strain limit than those of a conventional alloy such as a Co—Cr based alloy is required. In view of this, the present inventors have decided to develop a new alloy with the use of a 35NLT alloy being a Co—Cr based alloy as the base, while adding an appropriate metal element to the base.

As a specific investigation content, it was decided to adjust the overall alloy composition while another metal element is substituted for a part of the Ni making up the 35NLT alloy. In this investigation, the kind of a metal element to be newly added is selected, and further the attention was paid to balance the improvement of mechanical properties such as elastic modulus and the ensuring of X-ray visibility and workability. Further, as a result of the investigation, the present inventors have found a medical alloy, which has unprecedented mechanical properties and various characteristics by adjusting the composition of other constituent elements such as Ni while Pt (platinum) is added to a Co—Cr based alloy as an additional element, and thus have conceived the present invention.

That is, the present invention is an medical alloy, including Pt, Co, Cr, Ni, and Mo, in which the alloy includes 10 atom % or more and 30 atom % or less of Pt, 20 atom % or more and 31 atom % or less of Cr, 5 atom % or more and 24 atom % or less of Ni, 4 atom % or more and 8 atom % or less of Mo, the balance Co, and unavoidable impurities, and a ratio of the Ni content ($C_{Ni}$) to the Pt content ($C_{Pt}$), $C_{Ni}/C_{Pt}$ is 1.5 or less.

As described above, the present invention is an alloy (Pt—Co—Cr—Ni—Mo alloy) in which the overall composition is adjusted while Pt is added to a conventional Co—Cr based alloy (35NLT alloy). Hereinafter, the medical alloy of the present invention will be described in detail. First, each metal element constituting the alloy will be described.

(A) Alloy Composition of the Medical Alloy of the Present Invention

Pt: 10 Atom % or More and 30 Atom % or Less

Pt has an effect of improving mechanical strength and elastic modulus to a Co—Cr based alloy. Further, Pt has a large atomic weight and is a so-called heavy metal. Accordingly, Pt also has an effect of improving the X-ray visibility. If the Pt content is less than 10 atom %, the above-described effect of improving the characteristics is small. If the Pt content exceeds 30 atom %, an intermetallic compound such as Co—Pt is formed, and the workability is lowered. For this reason, it becomes difficult to produce a finely processed product such as extra-fine wire.

Pt has an effect of improving the above-described multiple characteristics, and therefore, is a characteristic and an essential constituent metal element for the alloy of the present invention. More preferably, the Pt content is 14 atom % or more and 30 atom % or less. This is for the purpose of maximizing the strength while the workability of an alloy is ensured. In addition, the corrosion resistance can be improved by relatively increasing the Pt content.

In this regard, Pt is a metal belonging to a precious metal, but other precious metals, Au and Ir are unsuitable as the additional elements for the alloy of the present invention. This is because the workability is largely lowered in the Co—Cr based alloy with the addition of Au and Ir. This point has been confirmed by preliminary tests conducted by the present inventors.

Cr: 20 Atom % or More and 31 Atom % or Less

Cr is an element that has an effect of improving the biocompatibility together with the improvement of the mechanical properties of an medical alloy. It is assumed to suppress the corrosion in the human body by forming a chemically stable Cr oxide layer on a surface of an alloy with the addition of Cr. If the Cr content is less than 20 atom %, the effect of the Cr oxide layer becomes insufficient. Further, if the Cr content is outside the above range, the mechanical properties also become insufficient. In addition, Cr has an effect of stabilizing the hcp phase of Co, and if the Cr content is excessive, the workability may be lowered. In consideration of the above situation, the appropriate range of the Cr concentration of the present invention is 20 atom % or more and 31 atom % or less.

Ni: 5 Atom % or More and 24 Atom % or Less

In the present invention, Ni has an important effect of ensuring the workability of an alloy. As described above, the present invention aims at improving the mechanical properties and the X-ray visibility with the substitution of Pt for Ni of the Co—Cr based alloy (35NLT alloy). However, Pt has an effect of lowering the workability, although not as much as Au, Ir, and Ta. Further, in an alloy in which Pt is substituted for the whole Ni of a Co—Cr based alloy, that is, an alloy not containing Ni, the workability is largely lowered, and it becomes difficult to process the alloy into a wire rod or the like. From the viewpoint of ensuring the workability of the alloy, it is essential to contain a proper amount of Ni. The reason why the Ni content is set to 5 atom % or more and 24 atom % or less is that the workability is significantly lowered if the Ni content is less than 5 atom %, and if the Ni content exceeds 24 atom %, there arises a problem that the elastic modulus is lowered to less than 240 GPa. In addition, as will be described later, it is required to have a certain relationship between the Ni content and the Pt content.

Mo: 4 Atom % or More and 8 Atom % or Less

In the alloy of the present invention, it is required to exhibit high strength and high elastic modulus, which are not found in conventional medical alloys. Mo is an essential constituent metal for ensuring such strength and elastic modulus. The Mo content is set to 4 atom % or more and 8 atom % or less. This is because if the Mo content is less than 4 atom %, the strength becomes the same degree as that of the conventional art, and if the Mo content exceeds 8 atom %, there arises a problem that the elastic modulus is lowered to less than 240 GPa.

Co: The Balance

The alloy of the present invention is an alloy newly developed on the basis of the Co—Cr based alloy (35NLT alloy). Therefore, Co is a basic constituent element of the alloy of the present invention. The matrix phase of Co has the mechanical and chemical properties of the alloy, and Co is an essential constituent metal for satisfying the minimum criteria required for the medical application. Further, the Co content is adjusted while the amount of Pt to be added is considered, and is defined as the balance of the alloy composition.

Relationship Between Ni Content and Pt Content

As described above, the medical alloy of the present invention is based on a Pt—Co—Cr—Ni—Mo alloy, and the range of the content of each constituent element is as described above. Here, in the present invention, certain requirements are set for the relationship between the Ni content and the Pt content, together with the composition range of each constituent metal. As described above, Pt is an essential metal element having an effect of improving the mechanical properties and X-ray visibility of the alloy, but there is a concern that Pt may be a factor for the decrease in workability. In view of this, the workability is ensured and improved with the containing of Ni in a certain amount or more. Therefore, Pt and Ni are constituent metals that are related to each other. Further, according to the investigation by the present inventors, the optimal mechanical properties and workability can be obtained with the setting of a certain requirement for the relationship between the Pt content and the Ni content, rather than the simple increase or decrease in both contents.

The certain requirement is that the ratio of the Ni content (CN) to the Pt content ($C_{Pt}$), $C_{Ni}/C_{Pt}$, is set to 1.5 or less. According to the present inventors, when the elastic modulus is observed with reference to the $C_{Ni}/C_{Pt}$ of the alloy, a peak occurs within a certain range. That is, an alloy having a $C_{Ni}/C_{Pt}$ exceeding 1.5 has an elastic modulus equal to or lower than that of the conventional art. In addition, the lower limit value of $C_{Ni}/C_{Pt}$ is preferably 0.17. If the $C_{Ni}/C_{Pt}$ is less than 0.17, there is a concern about the workability. The $C_{Ni}/C_{Pt}$ is more preferably 0.3 or more and 1.5 or less.

Optional Additional Element

The alloy of the present invention is based on a quinary alloy made of Pt, Co, Cr, Ni, and Mo, and may be made of these five elements only, but it is acceptable to optionally add the following specific additional elements.

W

According to the investigation by the present inventors, W, which is the same Group 6 element as Mo, is an additional element having an effect similar to that of Mo in the alloy of the present invention. That is, with the addition of W, the strength and the elastic modulus are expected to be improved. W, which is an optional additional element, can be added together with Mo, and is added so that the total of the W content and the Mo content is 4 atom % or more and 8 atom % or less. When W is added, the W content is preferably 0.01 atom % or more.

Fcc-Stabilizing Element

Co, which is a basic constituent element of the alloy of the present invention, is an element that exhibits an hcp structure at room temperature and undergoes a phase transformation to an fcc structure at a high temperature. The hcp structure affects the workability of the alloy because of being relatively brittle, and the fcc structure is ductiler. The phase transformation temperature of Co in the present invention fluctuates due to the alloying with other elements, but by lowering of the phase transformation temperature with a predetermined additional element (fcc-stabilizing element), the fcc structure can be stabilized. In this way, the workability of the alloy can be improved. Examples of the fcc-stabilizing element include Ti, V, Mn, Fe, Zr, Nb, and Ta. According to the investigation by the present inventors, when at least one of these elements is added to the alloy of the present invention in a total amount of 0.01 atom % or more and 10 atom % or less, the alloy is expected to have mechanical properties improved by such elements. However, if such elements are added in a total amount exceeding 10 atom %, the mechanical properties are deteriorated. Ni is predicted to be substituted for such elements. In this way, the workability of the alloy can be improved.

Any Other Additional Element

The alloy of the present invention can contain B, C, N, and Si in addition to the above-described W and fcc-stabilizing elements. These additional elements have a grain-boundary reinforcing action. B, C, N, and Si can be contained in a total amount of 0.01 atom % or more and 2 atom % or less. It is considered that B, C, N, and Si are contained in the alloy of the present invention by being substituted for a part of Co and Cr.

Impurity Elements

Further, the alloy of the present invention may contain unavoidable impurities. Examples of the unavoidable impurities of the alloy of the present invention include Al, P, S, Ca, Cu, and Ce, and the unavoidable impurities may be contained in a total amount of 0.01 atom % or more and 1 atom % or less. It is considered that the unavoidable impurity elements are contained in the alloy of the present invention by being substituted for a part of Co and Cr.

(B) Mechanical Properties of the Medical Alloy of the Present Invention

In the course of finding the present invention, the present inventors have simulated the deformation state, the load and the like of the medical device at each stage in a method of treatment with a medical device such as a flow-diverter stent.

For example, a stent such as a flow-diverter stent is a medical device formed by weaving a wire rod (wire) into a tube shape. A stent, with its inner diameter reduced, is inserted into a catheter, and is transferred together with the catheter to a treatment site (aneurysm, or the like) in a blood vessel. The stent that reached the treatment site is extruded from the catheter, and then expanded and placed in the blood vessel. The wire constituting the stent is loaded and deformed at each stage of the process.

In addition to the above stent, an embolic coil is produced by primary coil processing and secondary coil processing, and the elastic performance is utilized during use (during treatment). As described above, it is predicted that a medical device will be subjected to large deformation and stress loading during the production and use processes.

From the analysis results of the simulation when a medical device is applied, the present inventors have defined some criteria as the mechanical properties required for an medical alloy. Hereinafter, the required mechanical properties will be described. The medical alloy of the present invention satisfies such criteria.

Elastic Modulus (Young's Modulus)

In the treatment with a stent described above, the stent released and expanded in a blood vessel is fixed while adequately pressing the inner wall of the blood vessel with its elastic force. The stent is preferably placed stably at the treatment site, and an adequate expanding force is required. The force in the radial direction (expanding force) of the stent may be sometimes referred to as radial force.

The radial force of the stent can be controlled by the elastic modulus (Young's modulus) of the constituent materials. Further, from the analysis results of the present inventors, the preferable elastic modulus is 240 GPa or more. In this respect, the elastic modulus of the 35NLT alloy being a conventional Co—Cr based alloy is around 230 GPa. In the present invention, the elastic modulus can be adjusted to 240 GPa with the addition of Pt, the specification of $C_{Ni}/C_{Pt}$ (1.5 or less), and the appropriate addition of Mo. In this regard, the upper limit of the elastic modulus is not particularly limited, but is preferably 350 GPa or less.

Yield Stress

Further, it is also preferable that the yield stress (tensile yield stress) is improved as the basic mechanical property of an alloy material. The yield stress indicates the strength within the elastic range. Various kinds of medical devices are embedded in the human body, and are subjected to a stress due to the movement, pulsation, or beating of muscles, blood vessels, or the like over a long period of time. Under such a use environment, a high yield stress is required to continue to function without deformation or breakage. Specifically, the yield stress is preferably 1680 MPa or more. The alloy of the present invention can also satisfy the criterion.

Elastic Strain Limit (Elastic Limit)

The above-described elastic modulus and yield stress are known as the basic mechanical properties of alloy materials. In this regard, in the present invention, it is more preferable to improve other mechanical properties in consideration of the use as an medical alloy. For example, a stent is produced by weaving a wire-shaped alloy into a tube shape. Further, the stent before being inserted into the human body is inserted into a catheter with a reduced diameter. In the course of producing and using such a stent, a bending stress is generated and strain is accumulated on the alloy wire. If the accumulated strain exceeds the elastic limit, plastic deformation is generated at the site, and therefore, even if the stent is released from the catheter, the stent will not expand sufficiently, and the original function may not be exhibited.

In view of this, it can be deemed that it is more preferable to have a high elastic strain limit in the medical alloy in order to exhibit resistance to the strain accumulation. Specifically, the elastic strain limit is preferably 0.7% or more. The alloy of the present invention can also satisfy the criterion.

Rupture Stress

Further, in a medical device that is assumed to be plastically deformed, such as a balloon-expandable stent, an appropriate rupture stress is required in order to maintain the function without rupturing even after the plastic deformation.

Specifically, the balloon-expandable stent can be prepared with an alloy material in an annealed state, and therefore, the rupture stress in an annealed state (annealing conditions are, for example, 1000° C. for 1 hour) is preferably 1000 MPa or more. Further, the rupture stress in a state after processing is preferably 2000 MPa or more. The alloy of the present invention can also satisfy the criteria.

(C) Utility Form of the Medical Alloy of the Present Invention

The medical alloy of the present invention described above can be used in various forms such as a plate material, a bar, a square bar, a hollow bar material, and a wire rod as the constituent material for various kinds of medical devices. In particular, the medical alloy is often used in a form of a wire rod or of being woven with a wire rod, as of a stent, an embolic coil, a guide wire, or the like. The alloy of the present invention can be supplied and used as a wire rod thanks to the good workability.

The medical alloy of the present invention can be processed into an alloy wire rod having a diameter of 1.6 mm or less, and can be applied to various use. The preferable diameter of the Pt—Co alloy wire rod for medical use is preferably 0.2 mm or less, and more preferably 0.05 mm or less. In this regard, the lower limit value of the diameter of the alloy wire rod is preferably as small as possible, but is preferably 0.005 mm or more in consideration of the use and workability. It is preferable that the alloy wire rod has the above-described mechanical properties in a state after processing.

The medical alloy of the present invention described above can be applied to various kinds of medical devices. Examples of the medical device for which the present invention is particularly useful include stents such as flow-diverter stents, or stent retrievers, catheters such as balloon catheters, coil such as embolic coils, guide wires, delivery wires, dental braces, clasps, artificial tooth roots, clips, staples, bone plates, nerve stimulation electrodes, leads for pacemakers, and radiation markers.

In these examples, stents such as flow-diverter stents are prepared by weaving wire rods with a knitting machine. The embolic coil is an instrument that is placed in a cerebral aneurysm and embolizes the aneurysm hole, and is prepared by processing a wire rod into a coil shape with a winding machine. The stent retriever is prepared by preparing a pipe/tube material and then by forming through laser processing.

The medical alloy of the present invention can constitute at least a part or all of the above-described various kinds of medical implements, and components of medical devices.

(D) Method for Producing the Medical Alloy of the Present Invention

The medical alloy of the present invention can be produced through a general melting and casting step. In the melting and casting step, a molten alloy having a desired composition is prepared, and is cast to produce a mother alloy having an ingot shape or the like. The mother alloy having undergone the melting and casting step can be formed into a desired shape by appropriate combination of hot working, warm working, and cold working. The processing treatment is not particularly limited, and is, for example, swaging processing, forging processing, or rolling processing. In this regard, the mother alloy having undergone the melting and casting step may be subjected to a homogenization heat treatment in which heating is performed at a temperature of 750° C. or more and 1300° C. or less for 2 hours or more and 48 hours or less, and then subjected to a processing treatment.

Further, the alloy wire rod can be produced by wire drawing of the alloy material obtained by cast and processing as described above. The wire drawing is appropriately combined with swaging processing, or drawing processing (drawbench processing). The working ratio in one-time wire drawing (1 pass) is preferably 4% or more and 20% or less. In addition, the wire drawing can be performed by hot working. The processing temperature is preferably 500° C. or more and 1300° C. or less.

Advantageous Effects of the Invention

As described above, the alloy for medical use of the present invention has the mechanical properties and X-ray visibility required as the constituent material for medical devices, and further, the workability is ensured. The progress of the medical devices are remarkable, and there are medical devices that are used in severer environments and conditions than ever before, such as flow-diverter stents. The medical alloy of the present invention is also useful as a constituent material for the latest medical devices. Further, the Ni concentration is lower than that of the conventional 35NLT alloy, and as a result, the elution amount of Ni ions also reduces. That is, the medical alloy of the present invention is less likely to cause a Ni allergy, and has good biocompatibility.

DESCRIPTION OF EMBODIMENTS

Hereinafter, the embodiment of the present invention will be described. In the present embodiment, a plurality of Pt—Co based alloys (Pt—Co—Cr—Ni—Mo alloys) each having adjusted contents of Pt, Co, Cr, Ni, and Mo were produced. Subsequently, the mechanical properties (elastic modulus, elastic strain limit, and yield stress) of each alloy were measured, and further the X-ray visibility was evaluated.

[Alloy Production]

In the production of a Pt—Co based alloy, high-purity raw materials of respective metals were weighed and mixed with each other, and the mixture was melted and cast by argon arc melting to prepare an alloy ingot. Subsequently, the alloy ingot was heated at 1200° C. for 12 hours for homogenization treatment. After the homogenization heat treatment, a wire rod having a diameter of 3 mm was produced by hot swaging processing. With the use of this wire rod as a base material, a sample for a tensile test, a sample for measurement of an elastic modulus, and a sample for evaluation of X-ray visibility were produced.

In addition, the various kinds of alloys produced above were subjected to quantitative analysis in order to accurately grasp the alloy composition. In this analysis, a specimen having a length of 1 mm was collected from an alloy wire rod having a diameter of 0.5 mm in the middle of the processing, and was quantitatively analyzed by Spark ICP (trade name of device: RIGAKU SPECTRO-SASSY/CIROS-MarkII). The microscopic observation of the crystal structure was performed by the SEM-EDX analysis on cross sections of various kinds of alloy wires. The measurement points of the EDX analysis were set to 3 points or more for each sample. In all the samples, the difference between the ICP analysis value and the SEM-EDX analysis value was within ±20%, and local segregation and the like were not observed.

[Elastic Modulus Measurement]

The above-produced base material having a diameter of 3 mm was rolled to prepare a plate material (60 mm×10 mm, having a thickness of 1 mm), and the plate material was subjected to heat treatment for stress relief, and thus a sample for elastic modulus measurement was prepared. The heat treatment for stress relief was performed by the heating at 1200° C. for 4 hours in a vacuum electric furnace. The elastic modulus measurement was performed by a free resonance method under the room-temperature atmosphere with a room-temperature elastic modulus measuring device, JE-RT.

[Workability Evaluation and Tensile Test (Yield Stress Measurement)]

The above-produced base material having a diameter of 3 mm was subjected to cold wire drawing with a cemented carbide die to a diameter of 0.6 mm, and was further subjected to cold wire drawing with a diamond die to a diameter of 0.25 mm. In these cold wire-drawing workings, a carbon-based lubricant was used as a lubricant. In the working on this wire rod, the same step was repeatedly performed three times, and when the alloy cracked or broke even once during the working, the alloy was determined to have workability "defective (×)". Further, in all of the three workings, the alloy on which the cold wire-drawing working was successfully performed to a diameter of 0.25 mm was determined to have workability "good (○)".

A tensile test was conducted using the alloy wire rod produced by the above cold wire-drawing working as a sample for the tensile test. The tensile test was conducted with the use of a tensile testing machine for extra-fine wire (STROGRAPH E3-S manufactured by Toyo Seiki Seisaku-sho, Ltd.). The test conditions were set to be a gauge length of 150 mm, and a crosshead speed of 10 mm/min. In this tensile test, the yield stress was measured. Further, the elastic strain limit and the rupture stress were also measured at the same time.

[X-Ray Visibility Evaluation]

The above-produced base material having a diameter of 3 mm was rolled to prepare a plate material (10 mm×10 mm, having a thickness of 0.3 mm), and the plate material was used as a sample for X-ray visibility evaluation. This sample was subjected to an X-ray transmission test under the condition of 63 kv×2.4 mA using a mobile C-arm X-ray system (Siemens Japan GEN2). The evaluation for X-ray visibility was based on the Gray-Scale value of 35NLT (No. 12 in the following Table 1), which is a conventional alloy. Alloys having a value lower than that of 35NLT was determined to have X-ray visibility "good (○)", and alloys having a value higher than that of 35NLT was determined to have X-ray visibility "poor (×)".

The results of the evaluation tests conducted on the alloys, which have various kinds of compositions and produced in the present embodiment, are shown in Table 1. The evaluation test was also conducted on the 35NLT alloy being a conventional medical alloy.

TABLE 1

| | Composition (at %) | | | | | | | Mechanical property | | | | X-Ray visibility | Workability | Category |
|---|---|---|---|---|---|---|---|---|---|---|---|---|---|---|
| No. | Pt | Cr | Ni | Mo | Co | W | $C_{Ni}/C_{Pt}$ | Elastic modulus (GPa) | Yield stress (MPa) | Elastic strain limit (%) | Rupture stress (MPa)*[1] | | | |
| 1 | 29.98 | 23.94 | 5.24 | 5.82 | Balance | — | 0.17 | 242 | 2360 | 1.0% | 2411 | ○ | ○ | Example |
| 2 | 27.00 | 23.91 | 8.22 | 5.83 | Balance | — | 0.30 | 251 | 2325 | 0.9% | 2415 | ○ | ○ | |
| 3 | 20.35 | 23.85 | 14.87 | 5.79 | Balance | — | 0.73 | 282 | 2295 | 0.8% | 2385 | ○ | ○ | |
| 4 | 17.61 | 23.88 | 17.61 | 5.88 | Balance | — | 1.00 | 275 | 2159 | 0.8% | 2244 | ○ | ○ | |
| 5 | 14.84 | 23.82 | 20.38 | 5.94 | Balance | — | 1.37 | 270 | 2099 | 0.8% | 2171 | ○ | ○ | |
| 6 | 15.95 | 20.20 | 18.80 | 5.88 | Balance | — | 1.18 | 243 | 1965 | 0.8% | 2015 | ○ | ○ | |
| 7 | 15.11 | 30.58 | 18.12 | 5.88 | Balance | — | 1.20 | 253 | 2235 | 0.9% | 2281 | ○ | ○ | |
| 8 | 14.80 | 22.95 | 20.10 | 4.10 | Balance | — | 1.36 | 257 | 2085 | 0.8% | 2245 | ○ | ○ | |
| 9 | 14.20 | 22.90 | 19.30 | 7.90 | Balance | — | 1.36 | 249 | 2254 | 0.9% | 2298 | ○ | ○ | |
| 10 | 8.90 | 27.90 | 14.90 | 7.60 | Balance | — | 1.67 | 218 | 2120 | 1.0% | 2230 | ○ | ○ | Comparative Example |
| 11 | 35.22 | 23.83 | — | 5.78 | Balance | — | — | NA*[2] | | | | ○ | × | |

TABLE 1-continued

| | Composition (at %) | | | | | | | Mechanical property | | | | | | |
|---|---|---|---|---|---|---|---|---|---|---|---|---|---|---|
| | | | | | | | | Elastic modulus | Yield stress | Elastic strain | Rupture stress | X-Ray | | |
| No. | Pt | Cr | Ni | Mo | Co | W | $C_{Ni}/C_{Pt}$ | (GPa) | (MPa) | limit (%) | (MPa)*1 | visibility | Workability | Category |
| 12 | 33.20 | 23.81 | 4.35 | 5.88 | Balance | — | 0.13 | 231 | 2354 | 1.0% | 2369 | ○ | ○ | |
| 13 | 15.63 | 18.24 | 18.32 | 5.88 | Balance | — | 1.17 | 238 | 2010 | 0.8% | 2198 | ○ | ○ | |
| 14 | 15.67 | 33.53 | 19.22 | 5.88 | Balance | — | 1.23 | 214 | 2311 | 1.1% | 2344 | ○ | ○ | |
| 15 | 14.66 | 22.85 | 19.83 | 3.10 | Balance | — | 1.35 | 221 | 2085 | 0.9% | 2245 | ○ | ○ | |
| 16 | 14.80 | 22.89 | 20.10 | 8.28 | Balance | — | 1.36 | 211 | 2310 | 1.1% | 2398 | ○ | ○ | |
| 17 | 11.82 | 23.91 | 23.40 | 5.83 | Balance | — | 1.98 | 237 | 2013 | 0.8% | 2185 | ○ | ○ | |
| 18 | 10.21 | 23.85 | 25.01 | 5.85 | Balance | — | 2.45 | 231 | 1945 | 0.8% | 2007 | ○ | ○ | |
| 19 | 14.20 | 22.99 | 19.30 | 4.88 | Balance | 1.00 | 1.36 | 241 | 2052 | 0.9% | 2154 | ○ | ○ | Example |
| 20 | 14.20 | 22.94 | 19.30 | 4.00 | Balance | 4.00 | 1.36 | 242 | 2020 | 0.8% | 2088 | ○ | ○ | |
| 21 | — | 22.90 | 33.50 | 6.20 | Balance | — | — | 232 | 2068 | 0.9% | 2275 | X | ○ | Conventional Example |

*1Measurement value after cold working
*2A sample for tensile test could not be produced due to the breaking of wire during cold wire-drawing working.

From Table 1, all of the Pt—Co based alloys (No. 1 to No. 9, and No. 19 to No. 20), each of which is within the composition range specified in the present invention and has a suitable ratio ($C_{Ni}/C_{Pt}$) of the Ni content ($C_{Ni}$) to the Pt content ($C_{Pt}$), exhibited a suitable elastic modulus of 240 MPa or more and had favorable X-ray visibility and workability. Further, the elastic strain limit exceeded 0.7%. The measurement samples were alloy wire rods after cold working, and all of which had a rupture stress exceeding 2000 MPa. In this regard, it was also confirmed that the alloy of No. 5 had a rupture stress of 1000 MPa or more when the alloy wire rod was further annealed and a rupture stress was measured.

The alloys outside the specification of the present invention were inferior to the alloys of the above examples in any one of the properties.

The alloy of No. 21, which corresponds to the 35NLT alloy being a conventional example, had a low elastic modulus of less than 240 MPa and poor X-ray visibility. The present invention is an alloy having a suitable composition of other constituent elements such as Ni while Pt is added to the Co—Cr based alloy being a conventional alloy. However, the alloy having a low content of Pt even with the addition of Pt, such as the alloy of No. 10, had a clearly low elastic modulus, and the elastic modulus was lower than that of the conventional example (No. 21). Even if Pt is added, a proper amount should be added.

In addition, with regard to the action of Ni, the alloy (No. 11) without the addition of Ni had poor workability and failed to be processed into a wire rod. It can be deemed it is indispensable for the present inventive medical alloy to be processed into a wire rod or the like, and also deemed that Ni is essential for that purpose. However, even if Ni is added, when the additive amount of Ni is less than 5 atom % as in the alloy of No. 12, the elastic modulus is low even though the workability is improved. Therefore, it is considered that there is a proper range also for the additive amount of Ni.

In this regard, the ratio ($C_{Ni}/C_{Pt}$) of the Ni content (CN) to the Pt content ($C_{Pt}$) will be investigated. This investigation was performed with the comparison of the alloys of No. 1 to No. 5, No. 17, and No. 18, in each of which the contents of additional elements (Cr and Mo) other than Pt and Mo are approximated.

The alloy of No. 1 is an alloy having a composition in which the Pt content is in the vicinity of the upper limit and the Ni content is in the vicinity of the lower limit, and having the lowest value of $C_{Ni}/C_{Pt}$ ($C_{Ni}/C_{Pt}$=0.17). This alloy was evaluated as acceptable in terms of the elastic modulus, the workability, and the like. Further, the elastic modulus increases as the value of $C_{Ni}/C_{Pt}$ increases. However, as in the alloys of No. 17 and No. 18, when the $C_{Ni}/C_{Pt}$ exceeds the upper limit value (1.5) specified in the present invention and becomes in the vicinity of 2.0 or more, the elastic modulus decreases, and becomes less than 240 MPa. Therefore, the need to make the $C_{Ni}/C_{Pt}$ appropriate was confirmed even for an alloy having a composition range of the present invention.

In the present invention, Mo is also an essential constituent metal, and it can be understood that with the comparison of the alloys of No. 5, No. 8, No. 15, and No. 16, in each of which the contents of constituent elements other than Mo are approximated, the elastic modulus tends to be low regardless of whether the Mo content is high or low. In the Pt—Co based alloy (Pt—Co—Cr—Ni—Mo alloy) of the present invention, it can be confirmed that there is an optimal range of 4 atom % or more and 8 atom % or less for the amount of Mo.

In addition, in the present invention, W is mentioned as an element having an effect similar to that of Mo, but it was confirmed that even the alloy to which W had been added exhibited favorable strength, workability, and the like, from the results of the alloys of No. 19 and No. 20.

In addition, from the results of the alloys of No. 13 and No. 14, it was also confirmed that the elastic modulus was less than 240 MPa when the Cr content was outside the specified range of the present invention.

INDUSTRIAL APPLICABILITY

The medical alloy of the present invention is a Pt—Co based alloy having good mechanical properties, X-ray visibility, and workability. The present invention can be expected to be applied to stents such as flow-diverter stents, or stent retrievers, catheters such as balloon catheters, coils such as embolic coils, and various kinds of medical devices such as guide wires, delivery wires, dental braces, clasps, artificial dental roots, clips, staples, bone plates, nerve stimulation electrodes, leads for pacemakers, and radiation markers.

The invention claimed is:

1. An alloy for medical use, consisting of Pt, Co, Cr, Ni, and Mo, and unavoidable impurities, wherein
   an atomic content of Pt in the alloy is 10 atom % or more and 30 atom % or less,
   an atomic content of Cr in the alloy is 20 atom % or more and 31 atom % or less,
   an atonic content of Ni in the alloy is 5 atom % or more and 24 atom % or less,
   an atomic content of Mo is 4 atom % or more and 8 atom % or less, and
   Co constitutes the balance of the alloy; and
   wherein $C_{Ni}/C_{Pt}$, which is a ratio of the atomic content of Ni in the alloy ($C_{Ni}$) to the atomic content of Pt in the alloy ($C_{Pt}$), is 1.5 or less.

2. The alloy for medical use according to claim 1, wherein the atomic content of Pt in the alloy is 14 atom % or more and 30 atom % or less.

3. The alloy for medical use according to claim 2, wherein the alloy has an elastic modulus of 240 GPa or more, and a yield stress of 1680 MPa or more.

4. A stent, a catheter, a coil, a guide wire, a delivery wire, dental braces, a clasp, an artificial dental root, a clip, a staple, a bone plate, a nerve stimulation electrode, a lead for a pacemaker, or a radiation marker, comprising the medical alloy defined in claim 2.

5. A component of a medical device, comprising the medical alloy defined in claim 2.

6. The alloy for medical use according to claim 1, wherein the alloy has an elastic modulus of 240 GPa or more, and a yield stress of 1680 MPa or more.

7. A stent, a catheter, a coil, a guide wire, a delivery wire, dental braces, a clasp, an artificial dental root, a clip, a staple, a bone plate, a nerve stimulation electrode, a lead for a pacemaker, or a radiation marker, comprising the medical alloy defined in claim 6.

8. A stent, a catheter, a coil, a guide wire, a delivery wire, dental braces, a clasp, an artificial dental root, a clip, a staple, a bone plate, a nerve stimulation electrode, a lead for a pacemaker, or a radiation marker, comprising the medical alloy defined in claim 1.

9. A component of a medical device, comprising the medical alloy defined in claim 1.

10. An alloy for medical use, consisting of Pt, Co, Cr, Ni, Mo, W, and unavoidable impurities, wherein
    an atomic content of Pt in the alloy is 10 atom % or more and 30 atom % or less,
    an atomic content of Cr in the alloy is 20 atom % or more and 31 atom % or less,
    an atomic content of Ni in the alloy is 5 atom % or more and 24 atom % or less,
    a combined atomic content of Mo and W in the alloy is 4 atom % or more and 8 atom % or less, and
    Co constitutes the balance of the alloy, and
    wherein $C_{Ni}/C_{Pt}$, which is a ratio of the atomic content of Ni in the alloy ($C_{Ni}$) to the atomic content of Pt in the alloy ($C_{Pt}$), is 1.5 or less.

11. The alloy for medical use according to claim 10, wherein the alloy has an elastic modulus of 240 GPa or more, and a yield stress of 1680 MPa or more.

12. A stent, a catheter, a coil, a guide wire, a delivery wire, dental braces, a clasp, an artificial dental root, a clip, a staple, a bone plate, a nerve stimulation electrode, a lead for a pacemaker, or a radiation marker, comprising the medical alloy defined in claim 10.

13. A component of a medical device, comprising the medical alloy defined in claim 10.

14. An alloy for medical use, consisting of Pt, Co, Cr, Ni, Mo, W, and unavoidable impurities, wherein
    an atomic content of Pt in the alloy is 14 atom % or more and 30 atom % or less,
    an atomic content of Cr in the alloy is 20 atom % or more and 31 atom % or less,
    an atomic content of Ni in the alloy is 5 atom % or more and 24 atom % or less of Ni,
    an combined atomic content of Mo and W in the alloy is 4 atom % or more and 8 atom % or less of Mo and W, and
    Co constitutes the balance of the alloy, and
    wherein $C_{Ni}/C_{Pt}$, which is a ratio of the atomic content of Ni in the alloy ($C_{Ni}$) to the atomic content of Pt in the alloy ($C_{Pt}$), is 1.5 or less.

15. The alloy for medical use according to claim 14, wherein the alloy has an elastic modulus of 240 GPa or more, and a yield stress of 1680 MPa or more.

16. A stent, a catheter, a coil, a guide wire, a delivery wire, dental braces, a clasp, an artificial dental root, a clip, a staple, a bone plate, a nerve stimulation electrode, a lead for a pacemaker, or a radiation marker, comprising the medical alloy defined in claim 14.

17. A component of a medical device, comprising the medical alloy defined in claim 14.

* * * * *